US006946151B2

(12) United States Patent
Chatterji

(10) Patent No.: US 6,946,151 B2
(45) Date of Patent: *Sep. 20, 2005

(54) THERAPEUTIC COMPOSITIONS

(75) Inventor: Arun K. Chatterji, Neenah, WI (US)

(73) Assignee: Ayurvedic-Life International, LLC, Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/378,789

(22) Filed: Mar. 4, 2003

(65) Prior Publication Data

US 2004/0151783 A1 Aug. 5, 2004

Related U.S. Application Data

(63) Continuation-in-part of application No. 10/292,831, filed on Nov. 12, 2002.

(51) Int. Cl.$^7$ .................. A61K 35/78; A61K 35/00; A61K 9/00
(52) U.S. Cl. .............. 424/725; 424/400; 424/439; 424/774
(58) Field of Search ............... 424/400, 439, 424/725, 794, 774

(56) References Cited

U.S. PATENT DOCUMENTS

| | | | |
|---|---|---|---|
| 4,761,286 A | 8/1988 | Hiji | |
| 4,824,672 A | 4/1989 | Day et al. | |
| 4,883,788 A | 11/1989 | Day et al. | |
| 4,988,682 A | 1/1991 | Kozikowski | |
| 5,063,210 A | 11/1991 | Lange, III et al. | |
| 5,137,921 A | 8/1992 | Kensho et al. | |
| 5,176,937 A | 1/1993 | Kurihara et al. | |
| 5,178,899 A | 1/1993 | Kurihara et al. | |
| 5,242,693 A | 9/1993 | Kurihara et al. | |
| 5,244,887 A | 9/1993 | Straub | |
| 5,484,777 A | 1/1996 | Lange, III et al. | |
| 5,641,511 A | 6/1997 | Kuhrts | |
| 5,730,988 A | * 3/1998 | Womack | 424/774 |
| 5,773,427 A | 6/1998 | Day | |
| 5,900,240 A | 5/1999 | Tomer et al. | |
| 6,133,237 A | 10/2000 | Noll et al. | |
| 6,187,753 B1 | 2/2001 | Noll et al. | |
| 6,376,481 B1 | 4/2002 | Bruce et al. | |
| 6,455,068 B1 | 9/2002 | Licari | |
| 2001/0031744 A1 | * 10/2001 | Kosbab | 514/54 |

FOREIGN PATENT DOCUMENTS

WO  WO 95/10292  * 4/1995 .......... A61K/35/78

OTHER PUBLICATIONS

Kazumasa Shimizu, et al., "Suppression of Glucose Absorption by Some Fractions Extract from Gymnema sylvestre Leaves," J. Vet. Med. Sci., vol. 59 (4); pp. 245–251 (1997).
Harry G. Preuss, M.D., et al., "Comparative Effects of Chromium, Vanadium and Gymnema Sylvestre on Sugar–Induced Blood Pressure Elevations in SHR," Journal of American College of Nutrition. vol. 17 (2); pp. 116–123 (1998).
Yumiko Nakamura, et al., "Fecal Steroid Excretion is Increased in Rats by Oral Administration of Gymnemic Acids Contained in Gymnema sylvestre Leaves," J. Nutr., vol. 129, pp. 1214–1222 (1999).
K. Baskaran, et al., "Antidiabetic Effect of a Leaf Extract From Gymnema Sylvestre in Non–Insulin–Dependent Diabetes Mellitus Patients," Journal of Ethnopharmacology, vol. 30, pp. 295–305 (1990).
E.R.B. Shanmugasundaram, et al., "Use of Gymnema Sylvestre Leaf Extract in the Control of Blood Glucose in Insulin–Dependent Diabetes Melitus," Journal of Ethnopharmacology, vol. 30, pp. 265–279 (1990).
E.R.B. Shanmugasundaram, et al., "Possible Regeneration of the Islets of Langerhans in Streptozotocin–Diabetic Rats Given Gymnema Sylvestre Leaf–Extracts," Journal of Ethnopharmacology, vol. 30, pp. 281–294 (1990).
Y. Okabayashi, et al., "Effect of Gymnema sylvestre, R.Br. on Glucose Homeostasis in Rats," Diabetes Research and Clinical Practice, vol. 9 (2), pp. 143–148 (1990).
D. J. Joffe, "Effect of Extended Release Gymnema Sylvestre Leaf Extract . . . ," Diabetes in Control Newsletter, Issue 76 (1): pp. 1–4 (Oct. 30, 2001).
K. R. Shanmugasundaram, et al., Enzyme Changes and Glucose Utilization in Diabetic Rabbits: The Effect of Gymnema Sylvestre, R.Br., Journal of Ethnopharmacology. vol. 7. pp. 205–234 (1983).
S. K. Baveja, et al., "Examination of Natural Gums and Mucilages as Sustaining Materials in Tablet Dosage Forms—Part II," Indian Journal of Pharmaceutical Sciences, vol. 51 (4), pp. 115–118 (Mar., 1988).

* cited by examiner

Primary Examiner—Thurman K. Page
Assistant Examiner—Simon J. Oh
(74) Attorney, Agent, or Firm—Olson & Hierl, Ltd.

(57) ABSTRACT

An oral composition, suitable as a hypoglycemic agent, includes an isolate from the leaves of *Gymnema sylvestre*, having a specified molecular weight. The isolate has a molecular weight at least about 3000 Daltons as determined by molecular weight cut-off filtration. Glucose metabolism in a human patient can be regulated by dosage forms that contain the aforesaid isolate from the leaves of *Gymnema sylvestre*, in combination with a non-metabolizable, water-swellable polysaccharide such as the exudate of *Sterculia urens*, and a water-soluble polysaccharide such as guar gum. Optionally, the present oral compositions can include a physiologically acceptable calcium source, a physiologically acceptable metal carbonate salt, a physiologically acceptable chromium salt, and/or a physiologically acceptable vanadium compound. In addition, antioxidants such as ascorbic acid, cholecalciferol, d-α-tocopherol, the carotenoids, lycopene, lutein, and the like, can be included as well. The present compositions are useful for amelioration of cholesterolemia, obesity, chronic complications of diabetes and prophylaxis for patients predisposed to the foregoing.

23 Claims, No Drawings

THERAPEUTIC COMPOSITIONS

CROSS-REFERENCE TO RELATED APPLICATION

This application is a continuation-in-part of co-pending U.S. Ser. No. 10/292,831 filed on Nov. 12, 2002.

FIELD OF THE INVENTION

This invention relates to the regulation of glucose metabolism in a human patient with naturally occurring, plant-derived components.

BACKGROUND OF THE INVENTION

The concentration of glucose in the human bloodstream must be controlled within a relatively tight range (60–120 milligrams per deciliter of blood) to maintain normal health. If blood glucose drops too low, a condition known as hypoglycemia results, with symptoms such as faintness, weakness, headache, confusion and personality changes. Severe hypoglycemia can progress to convulsions, coma and death. Excessive blood glucose, or hyperglycemia, causes excess urine production, thirst, weight loss, fatigue, and in the most severe cases, dehydration, coma and death. Chronic hyperglycemia causes tissue damage due to the chemical reactions between the excess glucose and proteins in cells, tissues, and organs. This damage is thought to cause the diabetic complications of blindness, kidney failure, impotence, atherosclerosis, and increased vulnerability to infection.

The pancreas makes hormones that regulate the concentration of glucose in the blood. Insulin lowers blood glucose levels; when glucose level rises after a meal, the pancreas secretes insulin, which causes muscle and other tissues to take up glucose from the blood stream. Glucagon raises blood glucose levels; when blood glucose levels fall, the pancreas secretes glucagon to signal the liver to make stored glucose available.

A third glucose-regulating hormone, amylin, was discovered in 1987. Physiologists now generally consider that all three hormones play a role in the complex aspects of glucose metabolism. The chemical structure of amylin and its metabolic action on muscle and pancreas tissue has recently been elucidated. Amylin is said to work with insulin to moderate the glucose-lowering effects of insulin under certain circumstances, to help replenish liver glycogen after a meal, and to encourage the synthesis of fat from excess glucose. As a result, amylin, like glucagon, can raise the blood glucose level.

Diabetes mellitus is associated with continuous and pathologically elevated blood glucose concentration; it is one of the leading causes of death in the United States and is responsible for about 5% of all mortality. Diabetes is divided into two major sub-classes: Type I, also known as juvenile diabetes, or Insulin-Dependent Diabetes Mellitus (IDDM), and Type II, also known as adult onset diabetes, or Non-Insulin-Dependent Diabetes Mellitus (NIDDM).

According to the American Diabetes Association, there are over one million juvenile diabetics in the United States. Diabetes is a form of autoimmune disease. Autoantibodies produced by the patients completely or partially destroy the insulin producing cells of the pancreas. Juvenile diabetics must, therefore, receive exogenous insulin during their lifetime. Without treatment, excessive acidosis, dehydration, kidney damage, and death may result. Even with treatment, complications such as blindness, atherosclerosis, and impotence can occur.

There are more than five million Type II (adult onset) diabetics diagnosed in the United States. Type II disease usually begins during middle age; the exact cause is unknown. In Type II diabetics, rising blood glucose levels after meals do not properly stimulate insulin production by the pancreas. Additionally, peripheral tissues are generally resistant to the effects of insulin. The resulting high blood glucose levels (hyperglycemia) can cause extensive tissue damage. Type II diabetics are often referred to as insulin resistant. They often have higher than normal plasma insulin levels (hyperinsulinomia) as the body attempts to overcome its insulin resistance. Some researchers now believe that hyperinsulinomia may be a causative factor in the development of high blood pressure, high levels of circulating low density lipo-proteins (LDLs), and lower than normal levels of the beneficial high density lipo-proteins (HDLs). While moderate insulin resistance can be compensated for in the early stages of Type II diabetes by increased insulin secretion, in advanced disease states insulin secretion is also impaired. Treatments of Type II diabetes preferably address both insulin resistance and faulty insulin secretion.

Insulin resistance and hyperinsulinomia have also been linked with two other metabolic disorders that pose considerable health risks: impaired glucose tolerance and metabolic obesity. Impaired glucose tolerance is characterized by normal glucose levels before eating, with a tendency toward elevated levels (hyperglycemia) following a meal. According to the World Health Organization, approximately 11% of the U.S. population between the ages of 20 and 74 are estimated to have impaired glucose tolerance. These individuals are considered to be at higher risk for diabetes and coronary artery disease.

Obesity may also be associated with insulin resistance. A causal linkage among obesity, impaired glucose tolerance, and Type II diabetes has been proposed, but a physiological basis has not yet been established. Some researchers believe that impaired glucose tolerance and diabetes are clinically observed and diagnosed only later in the disease process after a person has developed insulin resistance and hyperinsulinomia.

Insulin resistance is frequently associated with hypertension, coronary artery disease (arteriosclerosis), and lactic acidosis, as well as related disease states. The fundamental relationship between these disease states, and a method of treatment, has not been established.

Insulin and sulfonylureas (oral hypoglycemia therapeutic agents) are the two major classes of diabetes medicines prescribed today in the United States. Insulin is prescribed for both Type I and Type II diabetes, while sulfonylureas are usually prescribed for Type II diabetics only. Sulfonylureas stimulate natural insulin secretion and reduce insulin resistance; these compounds do not replace the function of insulin in metabolism. Approximately one-third of patients who receive sulfonylurea become resistant to it. Some Type II diabetics do not respond to sulfonylurea therapy. Of patients who do respond to initial treatment with sulfonylureas, 5–10% are likely to experience a loss of sulfonylurea effectiveness after about ten years.

Insulin itself has a relatively narrow therapeutic window. Relatively high insulin doses can produce hypoglycemic shock as the blood glucose drops too low. Low or infrequent doses may result in hyperglycemia.

In Europe, two other classes of oral hypoglycemic agents are available, i.e., biguanides and alpha-glucosidase inhibitors. Biguanides work by reducing glucose production in the liver and limiting glucose absorption. Although biguanides are also used in Canada, they are banned in the U.S. due to increased incidence of mortality. Alpha-glucosidase inhibitors are sold in certain European countries, but have not obtained FDA approval for use in the U.S. These drugs reduce high blood glucose levels by slowing the uptake of ingested foods. Side effects include flatulence, diarrhea, and abdominal pain.

U.S. Pat. No. 4,761,286 to Hiji discloses that an aqueous extract derived from the leaves of Gymnema sylvestre can be utilized in combination with a foodstuff that is absorbed as glucose by the intestinal tract so as to inhibit glucose absorption. Chatterji, International Patent Application No. WO 95/10292, reported that glucose metabolism in a human patient can be effectively modulated by oral administration of an extract derived from the leaves of G. sylvestre in combination with a bio-inert polysaccharide, i.e., a polysaccharide that is non-metabolizable by the patient.

It has now been found, however, that glucose metabolism in a human patient can be effectively modulated by oral administration of a relatively high molecular weight isolate derived from the leaves of G. sylvestre, optionally in combination with a non-metabolizable, water-swellable polysaccharide and a water-soluble polysaccharide.

SUMMARY OF THE INVENTION

The present invention provides a relatively high molecular weight (HMW) isolate derived from Gymnema sylvestre leaves. The present invention also includes therapeutic dosage forms containing the isolate and a non-metabolizable, water-swellable polysaccharide, preferably a Sterculia urens exudate, preferably in a respective weight ratio in the range of 5:1 to about 1:5, more preferably about 1:2 to about 2:1, together with a water-soluble polysaccharide, preferably guar gum. The aforementioned isolate is obtainable by ethanolic extraction of Gymnema sylvestre leaves, followed by isolation of an insulinotropically active principle from the extract. The isolated insulinotropically active principle is a high molecular weight fraction having a molecular size of at least about 3000 Daltons, based on molecular weight cut-off filtration.

Another aspect of the present invention is a method for modulating glucose metabolism in a mammal, e.g. a human patient, a household pet, and the like, by orally administering to the mammal an effective amount of the aforesaid combination of ingredients which is sufficient to at least stabilize, and preferably reduce, the blood glucose level of the mammal.

The isolate of the present invention is useful as a dietary supplement, to delay the onset of diabetes, as an adjunct therapy with insulin for Type I diabetic patients to assist in blood sugar level control, and to reduce the likelihood of the onset of diabetes in those who are genetically predisposed to diabetes, cholesterolemia or obesity. The isolate of the present invention is also useful for the treatment of diabetic retinopathy, cholesterolemia, as well as chronic complications of diabetes such as cardiovascular diseases, decubitus ulcers, and the like.

DESCRIPTION OF PREFERRED EMBODIMENTS

Gymnema sylvestre is a plant that belongs to the family Asclepiadaceae. The plant grows principally in Central and Western India, in tropical Africa and in Australia. Aqueous extracts from the leaves of G. sylvestre have been reported to inhibit, temporarily, the taste of sweet substances. It has also been reported that the raw leaves of G. sylvestre have been used in India as a folk medicine for various afflictions including diabetes mellitus. Some fourteen or fifteen different compounds, all having a relatively lower molecular weight, are reported to have been isolated from the leaves of G. sylvestre by various techniques (see, e.g., Stocklin, J. Agr. Food Chem., 1969, 17(4):704–708 and Sinsheimer, J. Pharm. Sci., 1970, 59(5):622–628). U.S. Pat. No. 5,137,921 reports that Conduritol A, a low molecular weight monosaccharide (M.W. 146) isolated from the leaves of Gymnema sylvestre, is an active anti-diabetic agent. It has now been found, however, that the high molecular weight isolates of the present invention are potent, insulinotropically active components of G. sylvestre leaves.

Insulinotropically active principles of G. sylvestre leaves are obtained from an aqueous alcoholic extract of fresh G. sylvestre leaves by size selective filtration of the extract to isolate selected molecular weight, insulinotropically active fractions therefrom. In one preferred embodiment, the obtained isolate has a molecular weight of at least about 3000 Daltons, as determined by molecular weight cut-off (MWCO) filtration.

Preferably an extract is obtained by extraction of G. sylvestre leaves with a monohydric C1 to C4 alcohol, e.g., ethanol, isopropanol, and the like, most preferably aqueous ethanol. The insulinotropically active portion of the G. sylvestre extract is then isolated by molecular weight cut-off filtration. In particular, the active portion is isolated by filtration of an aqueous solution of the extract through a membrane having a molecular weight cut-off of about 3000 Daltons, and the material retained by the membrane (i.e., the retentate), which has a molecular weight of at least about 3000 Daltons, is collected and isolated.

The product of the present invention is preferably prepared by first soaking fresh leaves of G. sylvestre for at least about 4 hours at ambient temperature in an aqueous alcoholic solution, preferably an aqueous ethanolic solution containing about 40 volume percent of ethanol. In a preferred embodiment, the leaves are soaked in water for at least about 18 hours, and then ethanol is added to the water to obtain an ethanol concentration of at least about 40% by volume, and the soaking is continued in the resulting aqueous ethanol solution for at least about 4 hours thereafter. The resulting liquid extract is filtered to remove extraneous solids and distilled to drive off ethanol and produce an aqueous bottoms solution, which is then treated with sulfuric acid to lower the pH thereof to a value of no more than about 2 and to precipitate out acid-insoluble salts that had been produced. The precipitates are removed by filtration, and the filtrate is neutralized with sodium hydroxide. The neutralized extract is then concentrated, and purified to produce the isolate of the present invention, which is an insulinotropically active factor of G. sylvestre leaves having a molecular weight of at least about 3000 Daltons.

This isolate is then preferably lyophilized to enhance storage life, and optionally combined with a non-metabolizable, water-swellable polysaccharide such as Sterculia urens exudate, or a hydroxypropylmethylcellulose (HPMC), to produce an oral dosage form embodying the present invention. As used herein and in the appended claims, the term "non-metabolizable polysaccharide" refers to a polysaccharide that is not significantly metabolized by a human patient. Also suitable for the present purposes as a non-metabolizable polysaccharide are the partially esterified oligosaccharides and polysaccharides disclosed in U.S. Pat. No. 4,959,466 to White. Illustrative non-metabolizable, water-swellable polysaccharides include, for example, hydroxypropyl cellulose, cellulose hydrolysis products, starch hydrolysis products, oat fiber and the like. Preferably, the non-metabolizable polysaccharide is the dried exudate of the tree *S. urens*, found in India, and readily available commercially.

Illustrative water-soluble polysaccharides are guar gum, locust bean gum, xanthan gum, tragacanth gum, gum arabic, acacia gum, and the like.

The water-soluble polysaccharide constitutes at least about 10 percent by weight of the total polysaccharide content of the present oral compositions. Preferably, the weight ratio of the water-swellable polysaccharide to the water-soluble polysaccharide is in the range of about 1:1 to about 1:3, respectively. More preferably, the weight ratio is about 1:1.

Additionally, the present oral compositions can include a physiologically acceptable calcium source, a physiologically acceptable metal carbonate salt, a physiologically acceptable chromium salt, and/or a physiologically acceptable vanadium compound. Physiologically acceptable antioxidants can be included as well.

Illustrative calcium sources suitable for use in the present compositions are calcium salts of organic acids such as calcium citrate, calcium lactate, calcium gluconate, and the like.

Illustrative metal carbonate salts are the alkaline earth metal carbonates such as calcium carbonate and magnesium carbonate, the alkali metal carbonates and bicarbonates such as sodium carbonate, sodium bicarbonate, potassium carbonate, and potassium bicarbonate.

The insulinotropic properties of the present compositions can be enhanced by chromium ions and vanadate ions that can be supplied by chromium salts and vanadium compounds.

Illustrative chromium salts suitable for use in the present compositions are the chromium salts of organic acids such as chromium nicotinate, chromium picolinate, and the like, as well as inorganic chromium salts such as chromium vanadate $[C_2VO_4]$ which can provide the desired chromium ions as well as vanadate ions.

Illustrative vanadium compounds suitable for the present purposes are vanadyl sulfate $[(VO)_2SO_4)_3]$, orthovanadic acid $[H_3VO_4]$, and the like.

If desired, the present oral compositions can also include one or more physiologically compatible antioxidants suitable for present purposes such as ascorbic acid (Vitamin C), cholecaliciferol (Vitamin D), d-α-tocopherol (Vitamin E), the carotenoids such as β-carotene (Vitamin A), lycopene, lutein, and the like.

The isolate is preferably lyophilized and combined with the non-metabolizable polysaccharide in a weight ratio in the range of about 5:1 to about 1:5, more preferably about 2:1 to about 1:2, respectively. Most preferably, the weight ratio of the lyophilized isolate to the non-metabolizable polysaccharide is about 1:1.5. The resulting combination can then be filled into hard gelatin capsules for oral administration. A typical gelatin capsule embodying the present invention contains about 100 to about 200 milligrams of the lyophilized isolate and about 150 to about 300 milligrams of *S. urens* exudate.

The dosage and therapeutically effective amount to be administered to a human patient for modulating glucose metabolism of the patient will vary depending upon, inter alia, the age, weight and condition of the patient. The usual daily dosage is preferably in the range of about 200 milligrams to about 900 milligrams of the lyophilized isolate per day, preferably in conjunction with about 300 milligrams to about 1350 milligrams of non-metabolizable polysaccharide such as *S. urens* exudate.

As used herein, the term "therapeutically effective amount" means that amount of the isolate that will elicit the biological or medical response of a patient that is being sought by a clinician.

A preferred schedule of administration using capsules containing about 100 milligrams of the lyophilized isolate and about 150 milligrams *S. urens* exudate is provided in Table 1, below.

TABLE 1

Dosage Schedules

| Patient diagnosis | Dosage Schedule* |
|---|---|
| Hyperinsulinemia | 1–2 capsules b.i.d. |
| Type II diabetic (moderate) | 2 capsules b.i.d. |
| Type II diabetic (high) | 2–3 capsules t.i.d. |
| Type I diabetic (moderate) | 1 capsule b.i.d. |
| Type I diabetic (high) with insulin as adjunct therapy | 2 capsules t.i.d. |

*b.i.d. = 2 times per day; t.i.d. = 3 times per day

The present oral dosage forms are useful for treating hyperglycemia, for reducing serum cholesterol levels (i.e., for treating cholesterolemia) and also are eminently well suited as prophylactics for patients genetically pre-disposed toward diabetes, cholesterolemia or obesity. For example, expectant mothers identified as likely to be so pre-disposed on the basis of family history, can take oral doses of the aforedescribed lyophilized isolate throughout the full terms of their respective pregnancies. The likelihood of elevated blood sugar levels for the mothers and their newborn babies is greatly minimized in this manner. For expectant mothers, the preferred oral dosage is about 200 milligrams of the lyophilized isolate together with about 300 milligrams of *S. urens* exudate twice daily, i.e., a 500 milligram capsule, b.i.d., containing the lyophilized isolate of the present invention and the *S. urens* exudate in a respective weight ratio of about 2:3. The isolate of the present invention is also useful for the treatment of diabetic retinopathy.

In addition to the aforementioned dosage forms, the present oral compositions can also be incorporated into a nutrient drink mix powder, a health snack bar, and like products for oral consumption.

The isolate of the present invention can be evaluated for insulinotropic activity by a variety of procedures, well known in the art. For example, insulin producing cells can be treated with the isolate of the present invention and the insulin production of the cells can be monitored by the double antibody method of Morgan et al., *Diabetes* 12:115–126 (1963), the relevant disclosure of which is incorporated herein by reference. Rat insulinoma (RIN) cells are a convenient model for studying effects of pharmaceutical agents, such as the isolate of the present invention, on mammalian insulin production. RIN cells can be cultured in a glucose rich medium such as Dulbecco's Modified Eagle's Medium (D-MEM), which contains glucose (typically about 0.1 to about 0.5% by weight) and about 10% by weight of fetal calf serum (FCS), and which provides nutrients such as glucose, amino acids, and vitamins suitable for mammalian cell metabolism.

The present invention is further illustrated by the following non-limiting examples.

EXAMPLE 1

Preparation of Extract and Isolate

Fresh leaves of *Gymnema sylvestre* were purchased and identified by a botanist. The fresh leaves were soaked for about 18 hours in tap water (about 1 kg leaves/4 L tap water) at ambient temperature. Aqueous ethyl alcohol (about 90 volume percent ethanol) was added thereto in sufficient quantity to bring the net alcohol percent level to about 40% by volume, and the entire batch was distributed with stirring into ten Erlenmeyer flasks. Flasks were placed on a shaker table and shaken for about four hours.

The flask contents were filtered and the recovered liquid extract was distilled in several batches to remove ethyl alcohol. The obtained aqueous bottoms solutions were combined, and dilute sulfuric acid (about 1 to 2 molar) was added thereto to reach a final pH of about 2. A sludge composed of acid-insoluble salts was formed and was removed by filtration. Soluble salts of sodium and potassium, inherent from the leaves, remained in the filtrate. The filtrate was neutralized with dilute sodium hydroxide and deionized by passing through an ion exchange column. The resulting solution (eluate) was concentrated to a semi-solid light-brown mass (a "syrupy" mass the consistency of molasses) using a rotary flask equipped with a vacuum, with the rotary flask rotated at a 45 degree angle on a water bath heated to a temperature of about 55–70° C.

The semi-solid concentrate was then subjected to ultra-filtration using stirred Amicon filtration cells and molecular weight cut-off (MWCO) membranes. In particular, the obtained semi-solid concentrate was fractionated using 200 mL Amicon stirred ultrafiltration cells (Millipore Catalog No. 5123) and matching 3000 MWCO membranes (Millipore Catalog No. PLBC 06210) to obtain a permeate fraction having a molecular weight less than about 3000 Daltons and a retentate fraction (the isolate) having a molecular weight of at least about 3000 Daltons.

EXAMPLE 2

Bioassay of *Gymnema sylvestre* Isolate

The insulin-releasing activity of the obtained permeate and retentate of Example 1 were tested by radioimmunoassay (RIA) using an RIA kit (Catalog No. RI-13K) purchased from Linco Research, Inc., St. Louis, Mo., utilizing rat insulinoma (RIN-58) cells, I-125 labeled insulin, rat insulin antiserum, and the double antibody technique of Morgan et al., *Diabetes* 12:115–126 (1963). The main activity was found in the retentate, which has a MWCO of at least about 3000 Daltons.

Rat insulinoma cells (RIN-58) were plated in 6-well plates and grown in a tissue culture medium that contained glucose. At 80% confluence, the medium was replaced with a glucose-free medium. About 24 hours later, fresh serum-free medium containing 10 mM glucose was added along with the fraction to be assayed. The cells were incubated for 3 hours. Duplicate aliquots of 25 µl each were drawn from the wells for RIA. The assay results are reported in Table 2, below.

TABLE 2

Bioassay of Insulin-Releasing Activity

| Fraction | Activity |
| --- | --- |
| Retentate (MW ≧ 3000 Daltons) | 9.5 ng/mL |
| Permeate (MW < 3000 Daltons) | 2.35 ng/mL\ |

EXAMPLE 3

Insulinotropic Drink Mix Powder

An oral composition suitable for use as a drink upon dispersion in water is shown in Table 3, below:

TABLE 3

| Lyophilized *G. sylvestre* fraction* | 1 gram |
| --- | --- |
| *S. urens* exudate | 2.5 grams |
| Guar gum | 2.5 grams |
| Calcium citrate | 500 milligrams |
| Chromium nicotinate | 120 micrograms |
| Niacin (nicotinic acid) | 120 milligrams |

*Molecular weight ≧ 3000 Daltons

EXAMPLE 4

Insulinotropic Drink Mix Powder

An oral composition suitable for use as a drink upon dispersion in water is shown in Table 4, below:

TABLE 4

| Lyophilized *G. sylvestre* fraction* | 0.5 grams |
| --- | --- |
| *S. urens* exudate | 2.5 grams |
| Guar gum | 2.5 grams |
| Calcium citrate | 500 milligrams |
| Chromium nicotinate | 60 micrograms |
| Niacin (nicotinic acid) | 60 milligrams |

*Molecular weight ≧ 3000 Daltons

EXAMPLE 5

Nutrient and Insulinotropic Drink Mix Powder

A composition suitable for use as a nutrient drink upon dispersion in water and containing the indicated dosages of antioxidants, amino acids, minerals and enzymes is described in Table 5, below:

TABLE 5

Drink Mix Powder With Antioxidants

| Lyophilized *G. sylvestre* fraction* | 1 gram |
| --- | --- |
| *S. urens* exudate | 2.5 grams |
| Guar gum | 2.5 grams |
| Calcium citrate | 500 milligrams |
| Chromium nicotinate | 60–200 micrograms |
| Niacin (nicotinic acid) | 60–120 milligrams |
| CoEnzyme $Q_{10}$ | 50–100 milligrams |
| Pine Bark Extract | 10–20 milligrams |
| Inositol | 50 milligrams |
| L-proline | 150 milligrams |
| L-lysine.HCL | 150 milligrams |
| L-arginine.HCL | 50 milligrams |
| L-cystine.HCL | 50 milligrams |
| L-carnitine tartarate | 50 milligrams |
| Pantothenic acid | 50 milligrams |
| Biotin | 100 micrograms |
| Folic acid | 150 micrograms |
| Phosphorous (as sodium phosphate) | 50 milligrams |
| Iron (as ferrous gluconate) | 18 milligrams |
| Magnesium (as magnesium chloride) | 80 milligrams |
| Zinc (as zinc chloride) | 10 milligrams |
| Selenium (as sodium selenite) | 50–200 micrograms |
| Copper (as cupric gluconate) | 1 milligram |
| Manganese (as manganese citrate) | 2 milligrams |
| Molybdenum (as ammonium molybdate) | 10 micrograms |
| Potassium (as potassium chloride) | 50 milligrams |
| Vitamin A (β-carotene) | 5,000 I.U. |
| Vitamin C (ascorbic acid) | 50 milligrams |
| Vitamin E (d-α-tocopherol) | 400 I.U. |
| Vitamin $B_1$ (thiamine) | 10 milligrams |
| Vitamin $B_2$ (riboflavin) | 10 milligrams |
| Vitamin $B_6$ (pyridoxine · HCL) | 15 milligrams |
| Vitamin $B_{12}$ (cyanocobalamin) | 50 micrograms |
| Vitamin D | 400 milligrams |

*Molecular weight ≧ 3000 Daltons

If desired, the antioxidant properties of the composition of Table 5, can be enhanced by the addition of a further amount of CoEnzyme $Q_{10}$ as well as the additional ingredients set forth in Table 5A below.

TABLE 5A

Antioxidant Enhancement

| | |
|---|---|
| CoEnzyme $Q_{10}$ | 50 milligrams |
| Lycopene | 1–5 milligrams |
| Lutein | 1–3 milligrams |
| Silicon (as silicic acid) | 2 milligrams |
| Vanadium (as vanadyl sulfate) | 10 micrograms |
| Nickel (as nickel sulfate) | 5 micrograms |
| Boron (as boric acid) | 150–1000 micrograms |

*Molecular weight ≧ 3000 Daltons

EXAMPLE 6

Insulinotropic Drink Mix Powder

A drink mix powder well suited for treatment of diabetes and obesity is set forth in Table 6, below:

TABLE 6

| | |
|---|---|
| Lyophilized *G. sylvestre* fraction* | 2 grams |
| *S. urens* exudate | 3.5 grams |
| Guar gum | 2.5 grams |
| *Commiphora mukul* | 100 milligrams |
| Calcium citrate | 500 milligrams |
| Chromium nicotinate | 120 micrograms |
| Niacin (nicotinic acid) | 150 milligrams |

*Molecular weight ≧ 3000 Daltons

Other optional ingredients, one or more of which can be added to the formulations described in Tables 3, 4 and 5 above are extracts of *Andrographis paniculata* (about 50 milligrams), *Solanum nigram* (about 50 milligrams), *Phyruntus niruri* (about 50 milligrams), purified Silajit (about 50 milligrams), *Ocimum sanctum* (about 150 milligrams), *Withania somnifera* (about 100 milligrams), *Picrorrhiza kurroa* (about 75 milligrams), *Tinospora cordifolia* (about 250 milligrams), Cimicufuga (black cohosh) (about 500 milligrams), *Tribulus terrestris* (about 200 milligrams) and *Serensa repens* (about 100 milligrams).

The formulations presented in the aforementioned Tables represent preferred daily compositions, and as such it is generally preferred that the daily dosage is deployed equally, in two to four sub-divided amounts. For example, if these formulations are taken as capsules, it is preferred to have the preferred dosage form as two capsules, b.i.d. In the cases of the administration as a nutritional drink mix or a healthy snack bar, the preferred dosage form may conveniently be given as one packet of the drink mix powder or one bar, b.i.d. The patient and the health professional may choose to mix the choice of the delivery system, while still staying within the dosage levels of the preferred compositions. Also, depending on the patient's health condition and the need to control the disease or symptoms, or to provide prophylaxis therefor, the health professional may recommend an alternate dosage pattern, or patterns, over certain periods of time, while staying with the teachings of this invention.

The foregoing discussion and the examples are intended as illustrative of the present invention and are not to be taken as limiting. Still other variations within the spirit and scope of the present invention are possible and will readily present themselves to those skilled in the art.

I claim:

1. An oral composition, suitable as a hypoglycemic agent, which comprises
   a lyophilized ethanolic extract from the leaves of *Gymnema sylvestre* having a molecular weight of at least about 3000 Daltons, as determined by molecular weight cut-off filtration,
   a non-metabolizable, water-swellable polysaccharide; and
   a water-soluble polysaccharide;
   the water-soluble polysaccharide constituting at least about 10 percent by weight of the total polysaccharide content in the composition.

2. The oral composition in accordance with claim 1 further including a calcium source.

3. The oral composition in accordance with claim 2 wherein the calcium source is calcium citrate.

4. The oral composition in accordance with claim 1 further including a physiologically acceptable metal carbonate salt.

5. The oral composition in accordance with claim 4 wherein the metal carbonate salt is a member of the group consisting of calcium carbonate, magnesium carbonate, potassium carbonate, sodium carbonate, potassium bicarbonate, sodium bicarbonate, and a mixture thereof.

6. The oral composition in accordance with claim 1 further including a physiologically acceptable chromium salt.

7. The oral composition in accordance with claim 6 wherein the chromium salt is a member of the group consisting of chromium nicotinate, chromium picolinate, chromium vanadate, and a mixture thereof.

8. The oral composition in accordance with claim 1 further including a physiologically acceptable vanadium compound.

9. The oral composition in accordance with claim 8 wherein the vanadium compound is vanadyl sulfate.

10. The oral composition in accordance with claim 1 wherein the non-metabolizable, water-swellable polysaccharide is *Sterculia urens* exudate.

11. The oral composition in accordance with claim 1 wherein the water-soluble polysaccharide is guar gum.

12. The oral composition in accordance with claim 1 wherein the water-swellable polysaccharide is *Sterculia urens* exudate, the water-soluble polysaccharide is guar gum, and the water-swellable polysaccharide and the water-soluble polysaccharide are present in the composition in a respective weight ratio in the range of about 1:1 to about 1:3.

13. The oral composition in accordance with claim 1 wherein the water-swellable polysaccharide is *Sterculia urens* exudate, the water-soluble polysaccharide is guar gum, and the polysaccharides are present in the composition in a weight ratio of about 1:1.

14. The oral composition in accordance with claim 1 further including a physiologically compatible antioxidant.

15. A drink mix powder comprising the oral composition in accordance with claim 1.

16. A snack bar comprising the oral composition in accordance with claim 1.

17. A method for modulating glucose metabolism in a human patient which comprises orally administering to the patient the composition of claim 1 in an amount and at a frequency sufficient to maintain the patient's blood glucose level at a predetermined value.

18. A method for treating a human patient genetically predisposed toward diabetes which comprises orally administering to the patient the composition of claim 1 in an amount and at a frequency sufficient to maintain the patient's blood glucose level at a predetermined value.

19. A method for treating a human patient suffering from Type I diabetes and receiving insulin therapy which comprises orally administering to the patient, as an adjunct to insulin therapy, the composition of claim 1, in an amount and at frequency sufficient to maintain the patient's blood glucose level at a predetermined value.

20. A method for treating a human patient predisposed toward obesity which comprises orally administering to the patient a therapeutically effective amount of the composition of claim 1.

21. A method for treating diabetic retinopathy in a human patient which comprises orally administering to the patient a therapeutically effective amount of the composition of claim 1.

22. A method for modulating glucose metabolism in a mammal which comprises orally administering to the mammal the composition of claim 1 in an amount and at a frequency sufficient to maintain the patient's blood glucose level at a predetermined value.

23. A method for treating cholesterolemia which comprises administering to a patient in need of such treatment the composition of claim 1 in a therapeutically effective amount sufficient to reduce the patient's serum cholesterol level.

* * * * *